(12) United States Patent
Morgan et al.

(10) Patent No.: US 7,342,508 B2
(45) Date of Patent: Mar. 11, 2008

(54) TELEMETRY SYSTEM AND METHOD WITH VARIABLE PARAMETERS

(75) Inventors: Wayne Morgan, Northridge, CA (US); Phillip B. Hess, Los Angeles, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 687 days.

(21) Appl. No.: 10/746,004

(22) Filed: Dec. 26, 2003

(65) Prior Publication Data

US 2005/0149147 A1    Jul. 7, 2005

(51) Int. Cl.
*G08C 17/00* (2006.01)

(52) U.S. Cl. .............................. 340/870.1; 340/870.11; 340/870.27; 455/73; 455/103; 607/60; 607/65

(58) Field of Classification Search ............. 340/870.1, 340/870.2, 870.11, 870.27; 327/257, 258; 343/702, 718; 370/480; 455/103, 73; 607/59, 607/60, 61
See application file for complete search history.

(56) References Cited

U.S. PATENT DOCUMENTS

| | | | |
|---|---|---|---|
| 4,561,443 A | 12/1985 | Hogrefe et al. | |
| 5,264,843 A | 11/1993 | Silvian | |
| 5,630,836 A | 5/1997 | Prem et al. | |
| 6,301,504 B1 | 10/2001 | Silvian | |
| 6,940,466 B2 * | 9/2005 | Terry | 343/841 |

FOREIGN PATENT DOCUMENTS

WO    WO 94/24772    10/1994

OTHER PUBLICATIONS

PCT International Search Report as issued in International Application No. PCT/US2004/041857, Mailing date Apr. 18, 2005.

* cited by examiner

*Primary Examiner*—Jeffery Hofsass
*Assistant Examiner*—Sisay Yacob
(74) *Attorney, Agent, or Firm*—Foley & Lardner LLP

(57) ABSTRACT

A programmable telemetry circuit that may be programmed for high bandwidth, low Q; low bandwidth, high Q; or for other parameters. The programmable telemetry circuit may include a first coil; a high impedance path having a first node connected to a first node of the first coil; a low impedance path having a first node connected to the first node of the first coil; a capacitive path having a first node connected to a second node of the first coil; and an input path for coupling signals into the high impedance path, the low impedance path, and the capacitive path. The low impedance path may be connected in parallel with the high impedance path. The capacitive path may form a circuitous path with the high impedance path and the low impedance path. The programmable circuit may be programmed to select the high impedance path or the low impedance path.

48 Claims, 7 Drawing Sheets

TELEMETRY SYSTEM AND METHOD WITH VARIABLE PARAMETERS

BACKGROUND

1. Field of the Invention

Embodiments of the present invention relate to telemetry systems and, in particular, to remote controlled telemetry systems with variable parameters and to telemetry systems implanted in human bodies in which the bandwidth and Q, among other parameters, are variable.

2. Description of Related Art

The use of implantable devices to remedy medical conditions is becoming increasingly frequent as the size and cost of such devices shrink. Many people with medical conditions who, in the past, were burdened with the prospect of remaining close to an analytical or treatment device have newfound freedom with implantable devices that allow them to receive the analysis and/or treatment they need from the implantable device.

For example, in the past, many diabetics who have needed blood glucose analysis on a daily basis or even multiple times during a day and who have required insulin injections in response to the analysis have been limited in their freedom of movement due to the requirement of remaining close to the analysis and treatment equipment. Implantable devices have changed much of that. Now, because blood glucose sensors and insulin infusion pumps have reached a state where they may be implanted into the body of a diabetic, diabetics are able to maintain a normal lifestyle while still obtaining the necessary analysis and treatment needed to combat their diabetes, without concern that a blood glucose analyzing device or insulin and needles are close at hand.

While implantable medical devices have improved the lives of many people with medical conditions, the devices themselves have still imposed certain requirements on the people who use them. For example, many implantable devices operate in conjunction with an external controller. Typically, data, software or other information is transmitted and/or received between the controller and the implantable device. The transmission of information between a controller and an implantable device imposes certain requirements on the person with the implantable device. For example, because the data transmission and reception range of the implantable device is necessarily limited, primarily due to power limitations and safety concerns having to due with data transmission from within a human body, the person with the implantable device must remain in relatively close proximity to the controller, within inches, in some circumstances.

Moreover, because data transmission rates of implantable devices are limited, also due to power limitations, the transmission of large amounts of data can take an exceedingly long time. For example, if historical data is transferred from an implantable device to an external controller for review or analysis by a medical professional, the historical data may encompass up to 100 kybtes of data or more. Likewise, if new software for an implantable device is to be downloaded from a controller to the implantable device, possibly as a result of the analysis of the historical data, the new software may encompass tens of kbytes to hundreds of kbytes or more. The transmission and reception of data, software or other information encompassing tens of kbytes to hundreds of kbytes and more can impose inconvenient restrictions on the freedom of the person with the implantable device, restrictions that the implantable device was supposed to remedy.

Generally, in telemetry circuitry, data transmission range and data transmission rate have been at odds with each other. In telemetry applications where it is desirable that data transmission range be maximized, such as in an implantable device that is transmitting real time sensor data, for example, data transmission rate has been minimized. Conversely, in telemetry applications where it is desirable that data transmission rate be maximized, such as in an implantable device that is transmitting or receiving large amounts of data, for example, data transmission range has been minimized. In the past, telemetry circuit designers have been forced to decide on whether to design the telemetry circuit for maximum data transmission rate or maximum data transmission range. Alternatively, in the past, telemetry circuit designers have compromised and have tried to find a balance between data transmission rate and data transmission range, maximizing neither.

What is needed is telemetry circuitry that is programmable, i.e., programmable so that data transmission or reception range is maximized for those applications that require maximum data transmission or reception range and so that data transmission range is maximized for those applications that require maximum data transmission range. Embodiments of the present invention provide such programmable telemetry circuitry.

SUMMARY

It is therefore an object of embodiments of the present invention to provide a telemetry system that is useable and practical in a variety of applications. It is a further object of embodiments of the present invention to provide a telemetry system that can be adjusted for high bandwidth, low Q modes and low bandwidth, high Q modes, depending on the desired application. It is yet a further object of embodiments of the present invention to provide a telemetry system that can be programmed for data transmission at high data rates or data transmission at long distances. It is yet a further object of embodiments of the present invention to provide an implantable communication device having a variable impedance antenna that may require long range transmission for some communications and short range transmission for other communications. It is yet a further object of embodiments of the present invention to provide an implantable communication device having a variable impedance antenna that may be used in medical applications. It is yet a further object of embodiments of the present invention to provide a telemetry system having circuit parameters that can be adjusted or that are programmable.

According to embodiments of the present invention, a programmable circuit may include a first coil for transmitting an input signal; a high impedance path having a first node connected to a first node of the first coil; a low impedance path having a first node connected to the first node of the first coil; a capacitive path having a first node connected to a second node of the first coil; and an input path for coupling signals into the high impedance path, the low impedance path, and the capacitive path. The low impedance path may be connected in parallel with the high impedance path. The capacitive path may form a circuitous path with the high impedance path and the low impedance path. The programmable circuit may be programmed to select the high impedance path or the low impedance path.

The high impedance path may include a low impedance driver and a resistive element. The resistive element may be a resistor or a semiconductor. The low impedance driver may be a semiconductor. The low impedance path may also include a low impedance driver, which may be a semiconductor. The capacitive path may also include a low impedance driver, which may be a semiconductor. The first coil may be an inductor.

The programmable circuit may further include a second coil having a first node and a second node; a switch having a first node and a second node; and a resistive element having a first node and a second node. The second coil may be inductively coupled to the first coil. The first node of the switch may be connected to the first node of the second coil. The first node of the resistive element may be connected to the second node of the switch. The second node of the resistive element may be connected to the second node of the second coil. Closing the switch may increase a bandwidth of the programmable circuit. The second coil may be an inductor. The resistive element may be a resistor or a semiconductor.

According to an embodiment of the present invention, a telemetry circuit having programmable parameters may include a first coil for transmitting signals; a high impedance path having a first node connected to a first node of the first coil; a low impedance path having a first node connected to the first node of the first coil; a capacitive path having a first node connected to a second node of the first coil; a first switch for coupling signals into the high impedance path, the low impedance path, and the capacitive path; a second switch having a first node and a second node; a high bandwidth, low Q filter having a first node and a second node; and a low bandwidth, high Q filter having a first node and a second node.

The low impedance path may be connected in parallel with the high impedance path. The capacitive path may form a circuitous path with the high impedance path and the low impedance path. The first node of the second switch may be connected to the second node of the first coil. The first node of the high bandwidth, low Q filter may be connected to the second node of the second switch.

The first node of the low bandwidth, high Q filter may be connected to the second node of the second switch. The second node of the high bandwidth, low Q filter may be connected to the second node of the low bandwidth, high Q filter such that the high bandwidth, low Q filter and the low bandwidth, high Q filter are connected in parallel.

The programmable circuit may be programmable to select the high impedance path or the low impedance path. The high bandwidth, low Q filter may be selected via the second switch when the high impedance path is selected and the low bandwidth, high Q filter may be selected via the second switch when the low impedance path is selected.

The high impedance path may include a low impedance driver and a resistive element. The resistive element may be a resistor or a semiconductor. The low impedance driver may be a semiconductor. The low impedance path may include a low impedance driver, which may be a semiconductor. The capacitive path may include a low impedance driver, which may be a semiconductor. The capacitive path may also include a capacitor. The first coil may be an inductor.

The telemetry circuit may further include a second coil having a first node and a second node; a switch having a first node and a second node; and a resistive element having a first node and a second node. The second coil may be inductively coupled to the first coil, the first node of the switch may be connected to the first node of the second coil, the first node of the resistive element may be connected to the second node of the switch, and the second node of the resistive element may be connected to the second node of the second coil. Closing the switch may increase a bandwidth of the programmable circuit.

According to an embodiment of the present invention, a method for modifying circuit parameters of a telemetry circuit may include providing a first coil for transmitting an input signal, the first coil having a first node and a second node; providing a high impedance path having a first node and a second node; providing a low impedance path having a first node and a second node, the low impedance path connected in parallel with the high impedance path; providing a capacitive path having a first node and a second node; the first node of the capacitive path connected to a second node of the first coil; providing an input path for coupling signals into the high impedance path, the low impedance path, and the capacitive path; connecting the first node of the first coil to the first node of the high impedance path and the first node of the low impedance path; connecting the first node of the capacitive path to the second node of the first coil; connecting the capacitive path to the high impedance path and the low impedance path such that the capacitive path forms a circuitous path with the high impedance path and the low impedance path; and enabling either the high impedance path or the low impedance path.

The high impedance path may include a low impedance driver and a resistive element. The resistive element may be a resistor or a semiconductor. The low impedance driver may be a semiconductor. The low impedance path may also include a low impedance driver, which may be a semiconductor. The capacitive path may also include a low impedance driver, which may be a semiconductor. The first coil may be an inductor.

The method may further include providing a second coil having a first node and a second node; providing a switch having a first node and a second node; providing a resistive element having a first node and a second node; inductively coupling the second coil to the first coil; connecting the first node of the switch to the first node of the second coil; connecting the first node of the resistive element to the second node of the switch and the second node of the resistive element to the second node of the second coil; and closing the switch to increase a bandwidth of the telemetry circuit.

The method may further include providing a high bandwidth, low Q filter having a first node and a second node; providing a low bandwidth, high Q filter having a first node and a second node; connecting the first node of the high bandwidth, low Q filter to the second node of the first coil; connecting the first node of the low bandwidth, high Q filter to the second node of the first coil; connecting the second node of the high bandwidth, low Q filter to the second node of the low bandwidth, high Q filter such that the high bandwidth, low Q filter and the low bandwidth, high Q filter are connected in parallel; programming the telemetry circuit to select the high impedance path or the low impedance path; and programming the telemetry circuit to select the high bandwidth, low Q filter when the high impedance path is selected and to select the low bandwidth, high Q filter when the low impedance path is selected.

According to an embodiment of the present invention, an implantable communication device having a variable impedance antenna may include a first coil for transmitting an input signal; a high impedance path having a first node connected to a first node of the first coil; a low impedance path having a first node connected to the first node of the first coil, the low impedance path connected in parallel with the high impedance path; a capacitive path having a first node connected to a second node of the first coil, the capacitive path forming a circuitous path with the high impedance path and the low impedance path; and an input path for coupling signals into the high impedance path, the low impedance path, and the capacitive path. The first coil may be an inductor. The implantable communication device may be programmed to select the high impedance path for short range communication and the low impedance path for long range communication. The implantable communication device may be implanted internally in a human body.

The high impedance path may include a low impedance driver and a resistive element. The resistive element may be a resistor. The resistive element may be a semiconductor. The low impedance driver may be a semiconductor.

The low impedance path may include a low impedance driver. The low impedance driver may be a semiconductor. The capacitive path may include a low impedance driver. The low impedance driver may be a semiconductor. The capacitive path may include a capacitor.

The implantable communication device may also include a second coil having a first node and a second node, the second coil being inductively coupled to the first coil; a switch having a first node and a second node, the first node of the switch being connected to the first node of the second coil; and a resistive element having a first node and a second node, the first node of the resistive element being connected to the second node of the switch, the second node of the resistive element being connected to the second node of the second coil. Closing the switch may increase a bandwidth of the programmable circuit. The second coil may be an inductor. The resistive element may be a resistor or a semiconductor.

The implantable communication device may also include an external controller inductively coupled to the implantable communication device. The external controller may transmit signals to the first coil and receive signals from the first coil.

DETAILED DESCRIPTION

In the following description of preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the preferred embodiments of the present invention.

Although the following description is directed primarily toward telemetry systems in which the bandwidth and Q are variable, embodiments of the present invention may be implemented in a variety of ways and used in a variety of capacities and applications. For example, embodiments of the present invention may be implemented in such a way such that other parameters of the telemetry circuit, such as the power output or transmit distance, for example, are variable. Also, embodiments of the present invention may be used in various applications, such as, for example, implantable medical devices, manufacturing applications, industrial applications, consumer applications and the like. Generally, embodiments of the present invention may be adapted for use in any environment or in any application in which data is being transmitted and received.

Figure 1:
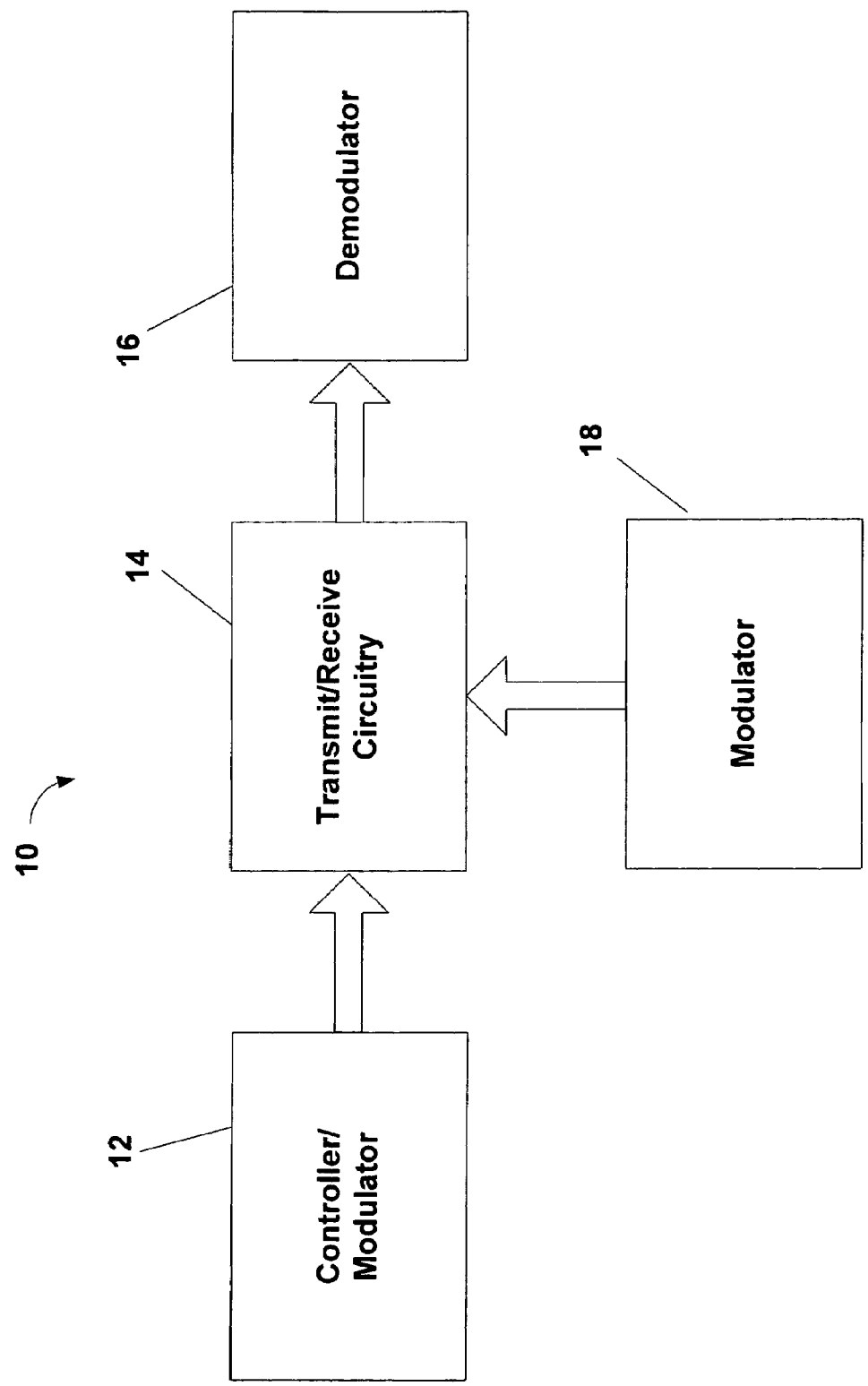
FIG. 1 shows a generalized block diagram of telemetry system according to an embodiment of the present invention.

FIG. 1 shows a generalized block diagram of a telemetry system 10 according to an embodiment of the present invention. The telemetry system 10 includes, but is not limited to, a controller/modulator 12, transmit/receive circuitry 14, a demodulator 16 and a modulator 18.

The controller/modulator 12 may be a remote device and may couple signals inductively to the transmit/receive circuitry 14. The signals coupled from the controller/modulator 12 to the transmit/receive circuitry 14 may be data signals or may be control and command signals.

Signals may be transmitted by inductive coupling from the controller/modulator 12 to the transmit/receive circuitry 14 in a variety of ways. For example, signals originating at the controller/modulator 12 may be sent via pulse code modulation to the transmit/receive circuitry 14. Other modulation schemes may be employed as well. For example, signals transmitted from the controller/modulator 12 may be modulated via amplitude modulation, frequency modulation, or any modulation scheme that is common in the art.

The transmit/receive circuitry 14 may send signals that it receives from the controller/modulator 12 to the demodulator 16 for demodulation. Demodulation may be accomplished in a variety of ways and will be consistent with the modulation scheme used to modulate the signals as they originated from the controller/modulator 12. The demodulator 16 may be fabricated on the same circuit as the transmit/receive circuitry 14 or may be implemented as an independent device. The demodulator 16 may be implemented with discrete components or may be implemented as a hybrid circuit or an ASIC. The demodulator 16 may be fabricated in a variety of ways that are common in the art.

Also, the modulator 18 may be fabricated on the same circuit as the transmit/receive circuitry 14 or may be implemented as an independent device. The modulator 18 may be implemented with discrete components or may be implemented as a hybrid circuit or an ASIC. The modulator 18 may be fabricated in a variety of ways that are common in the art.

The transmit/receive circuitry 14 may be fabricated in a variety of ways as well. For example, the transmit/receive circuitry 14 may be implemented with discrete components, as a hybrid circuit or may be fabricated as an application specific integrated circuit (ASIC).

Figure 2:
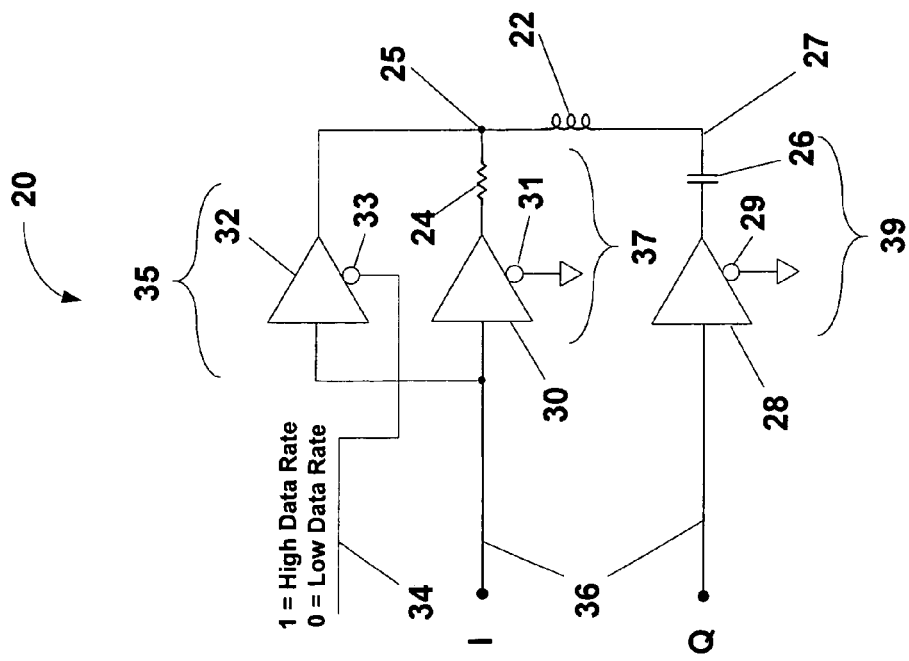
FIG. 2 shows a schematic diagram of a transmit circuit according to an embodiment of the present invention.

FIG. 2 shows a transmit circuit 20 according to an embodiment of the present invention. The transmit circuit 20 includes, but is not limited to, a first coil 22, a resistive element 24, a capacitive element 26, low impedance drivers 28, 30 and 32, an enable line 34 and an input path 36. The combination of the capacitive path driver 28 and the capacitive element 26 forms a capacitive path 39. The capacitive path 39 connects to the first coil at a second node 27. The low impedance driver 30 along with the resistive element 24 forms a high impedance path 37. The high impedance path 37 connects to the first coil 22 at a first node 25. The low impedance driver 32 in and of itself forms a low impedance path 35. The low impedance path 35 connects to the first coil 22 also at the first node 25. In addition, the low impedance path 35 is connected in parallel with the high impedance path 37. The low impedance drivers 28, 30 and 32, along with the resistive element 24 and the capacitive element 26, form a circuitous path between the low impedance path 35, the high impedance path 37, the capacitive path 39 and the first coil 22.

According to an embodiment of the present invention, the transmit circuitry 20 shown in FIG. 2 may be operated by supplying I and Q symbols at the input path 36. The I and Q symbols may be generated at another portion of the transmit circuitry 20 (not shown) or may be derived from the controller/modulator 12 shown in FIG. 1. Each of the low impedance drivers 28, 30 and 32 may include enable pins 20 which, in the embodiment of the invention shown in FIG. 2, are active low enable pins. The enable pins for the low impedance drivers 28 and 30 are grounded in the embodiment of the invention shown in FIG. 2. Thus, the low impedance drivers 28 and 30 are always enabled. The capacitive path low impedance driver 28 is generally not affected by the high impedance path driver 30 or the low impedance path driver 32. Thus, the Q symbol or any other signal placed on the input path 36 to the capacitive path driver 28 is immediately processed by the transmit circuit and appears at the first coil 22 where it will be transmitted.

Although the enable pin 20 of the high impedance path driver 30 is also grounded, the operation of the high impedance path 37 is affected by the low impedance path 35 because the high impedance path 37 and the low impedance path 35 are connected in parallel. If a high data rate mode is chosen, a logic "1" or a high signal is placed upon the enable line 34, effectively disabling the low impedance path driver 32. Accordingly, the low impedance path 35 is effectively eliminated from the circuit and the I symbol or any other signal placed upon the input line 36 appears at the high impedance path driver 30 and is processed by the transmit circuit 20. The signal then appears at the first coil 22 where it may be transmitted.

However, if a low data rate mode is chosen, a logic "0" or a low signal is placed upon the input line 34, thereby enabling the low impedance path driver 32. Because the low impedance path is connected in parallel with the high impedance path, the low impedance path effectively short circuits the high impedance path. Thus, the I symbol or any other signal that appears on the input line 36 will be processed by the low impedance path driver 32 and will appear at the first coil 22 where it may be transmitted.

The low impedance path 35, the high impedance path 37, and the capacitive path 39 may be implemented in a variety of ways. For example, the low impedance drivers 28, 30 and 32 may be standard semiconductor low impedance drivers that are common in the art. The first coil 22 may be an inductor or may be fabricated using semiconductors or other components, such as in, for example, a generalized impedance converter circuit. The resistive element 24 may be a resistor, a transistor or other semiconductor. The capacitive element 26 may be a capacitor, a bipolar transistor, a field effect transistor or some other semiconductor.

Figure 3:
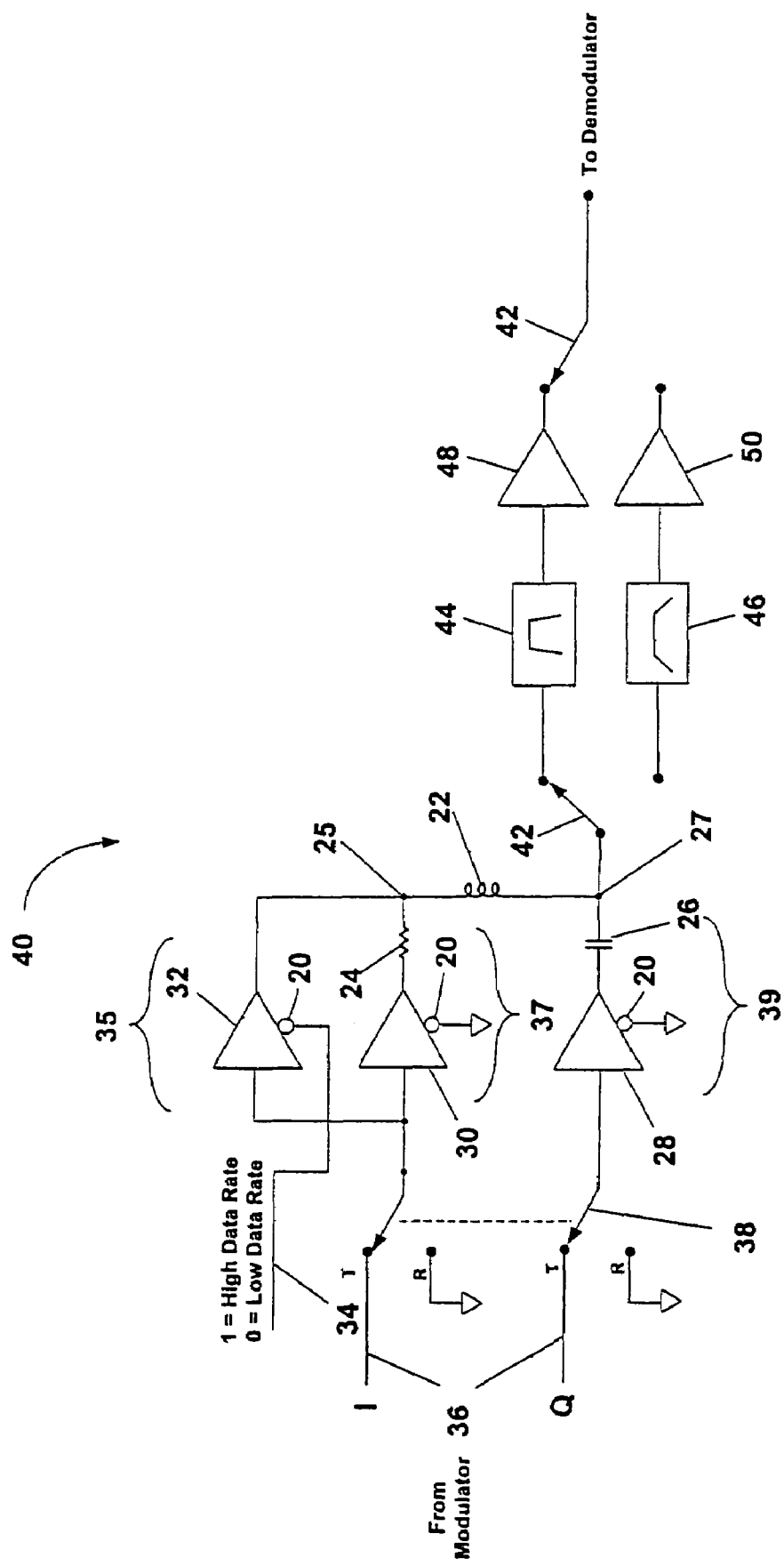
FIG. 3 shows a schematic diagram of a transmit/receive circuit according to an embodiment of the present invention.

FIG. 3 shows a transmit/receive circuit 40 according to an embodiment of the present invention. In the embodiment of the invention shown in FIG. 3, the transmit circuitry is similar to that shown in the embodiment of the invention of FIG. 2. However, in order to differentiate between transmit and receive modes, a switch 38 has been placed in series with the input path 36. Thus, the capacitive path driver 28 and the high impedance path driver 30 may be switched between transmit and receive nodes depending on the mode chosen for the circuit. The switch 38 may be a ganged switch or some other switch that is common in the art. The switch 38 may be programmable and may respond to signals originating at the controller/modulator 12 shown in FIG. 1, or may respond to signals originating elsewhere.

In addition, the second node 27 is connected to a second switch 42 which is used to switch between a high data rate path and a low data rate path. The high data rate path may include, but is not limited to, a high bandwidth, low Q filter 46 and a high bandwidth amplifier 50. The low data rate path may include, but is not limited to, a low bandwidth, high Q filter 44 and a low bandwidth amplifier 48.

The second switch 42 may be a ganged switch and may operate in conjunction with the enable line 34. Thus, when a high data rate is selected by placing a logic "1" or a high signal on the enable line 34, the high data rate path, which may include the high bandwidth, low Q filter 46 and the high bandwidth amplifier 50, is switched into the circuit using the second switch 42. Likewise, when a low data rate is selected by putting a logic "0" or a low signal on the enable line 34, the low data rate path, which may include low bandwidth, high Q filter 44 and a low bandwidth amplifier 48, is switched into the circuit using the second switch 42. The second switch 42 may also be programmable and may respond to signals originating at the controller/modulator 12 shown in FIG. 1, or may respond to signals originating elsewhere.

The high bandwidth, low Q filter 46 and the low bandwidth, high Q filter 44 may be implemented in a variety of ways. For example, according to an embodiment of the present invention the high bandwidth, low Q filter 46 and the low bandwidth, high Q filter may be implemented as analog or digital filters. According to another embodiment of the present invention, the high bandwidth, low Q filter 46 and the low bandwidth, high Q filter may be implemented in a digital signal processor. The high bandwidth amplifier 50 and low bandwidth amplifier 48 may be implemented with standard amplifiers that are common in the art or may be integrated as custom designed amplifiers.

Figure 4:
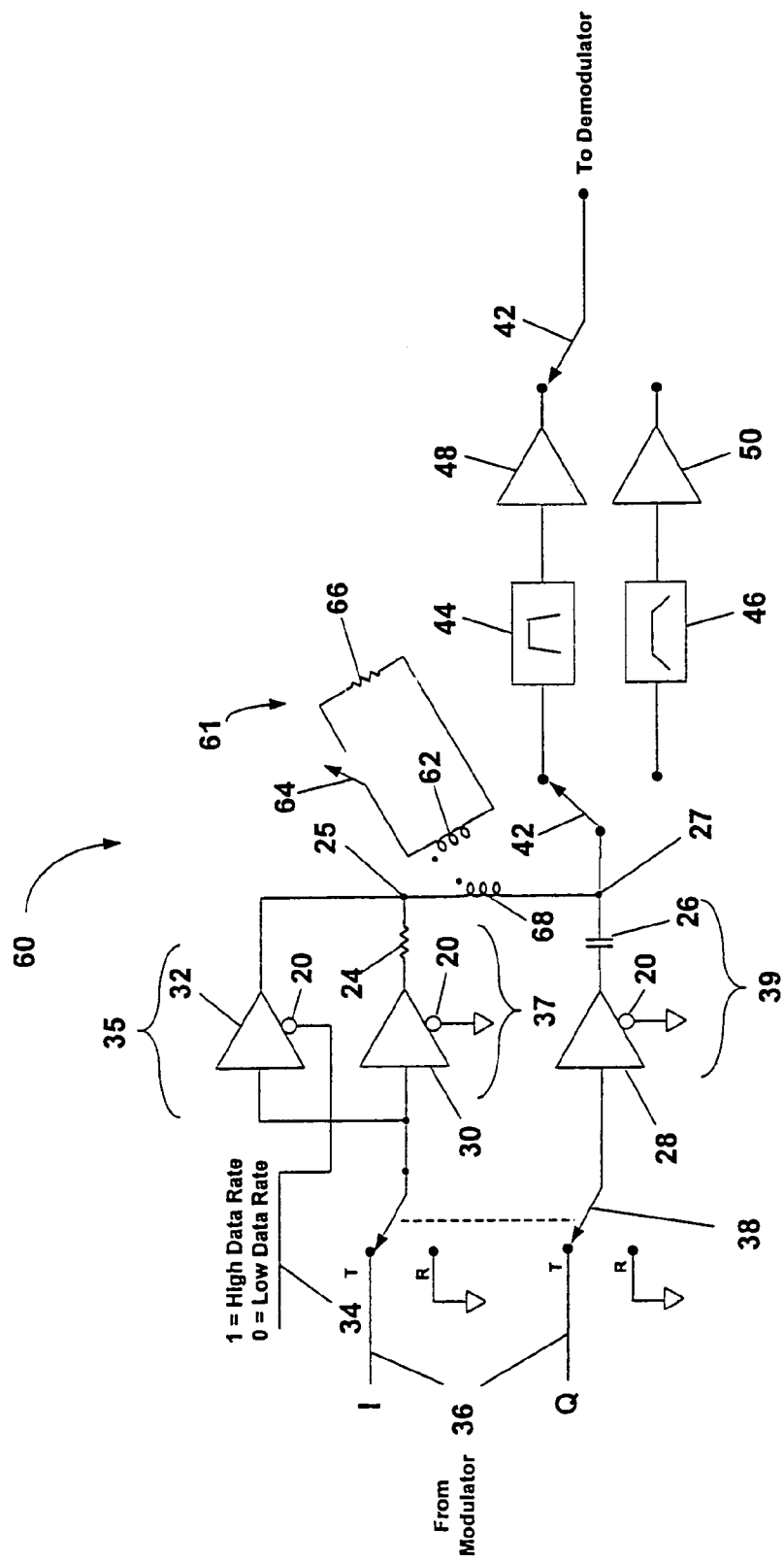
FIG. 4 shows a schematic diagram of a transmit/receive circuit according to another embodiment of the present invention.

FIG. 4 shows a transmit/receive circuit 60 according to another embodiment of the present invention. The transmit/receive circuit 60 shown in FIG. 4 is similar to the transmit/receive circuit 40 shown in FIG. 3. However, the transmit/receive circuit 60 of FIG. 4 includes an inductively coupled high impedance circuit 61 that includes, without limitation, a second inductively coupled coil 62, a third switch 64 and a resistive element 66. When a high data rate is needed, the high impedance circuit 61 may be selected instead of or in addition to the high impedance path 37 consisting of the high impedance path driver 30 and the resistive element 24.

In operation, if the high impedance circuit 61 is selected, the third switch 64 will close forming the high impedance circuit 61 which is inductively coupled via the second inductively coupled coil 62 to the first inductively coupled coil 68. The third switch 64 may be programmable and may respond to signals originating at the controller/modulator 12 shown in FIG. 1, or may respond to signals originating elsewhere.

Figure 5:
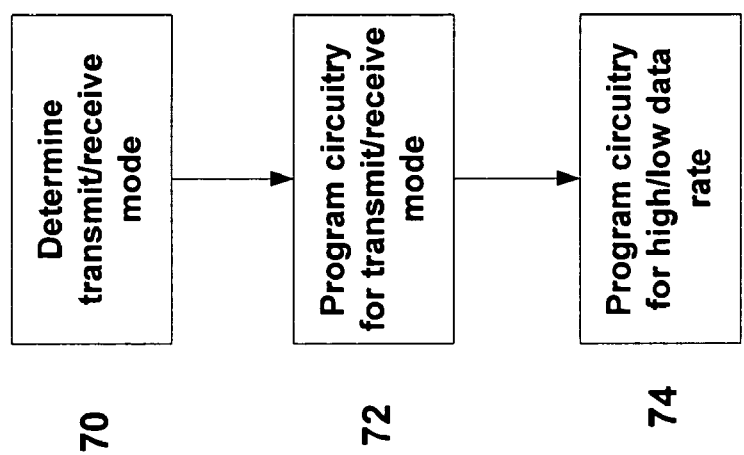
FIG. 5 shows a method of using a telemetry circuitry according to an embodiment of the present invention.

A generalized method of using the telemetry circuitry shown in FIGS. 1-4 according to an embodiment of the present invention is seen in FIG. 5. In FIG. 5, at step 70, a transmit or receive mode is determined. A transmit mode may be desired, for example, in situations where data that has been stored in the telemetry circuitry is required for analysis by an attending medical professional. Likewise, a receive mode may be desired, for example, in situations where a medical professional has analyzed data stored in the telemetry circuitry and wants to send programming information to the telemetry circuitry based on his or her analysis.

At step 72, the controller is programmed for either transmit or receive mode depending on the application desired. Likewise, at step 74, the controller is programmed for a high or a low data rate depending on the desired application, as is discussed in more detail below.

Figure 6:
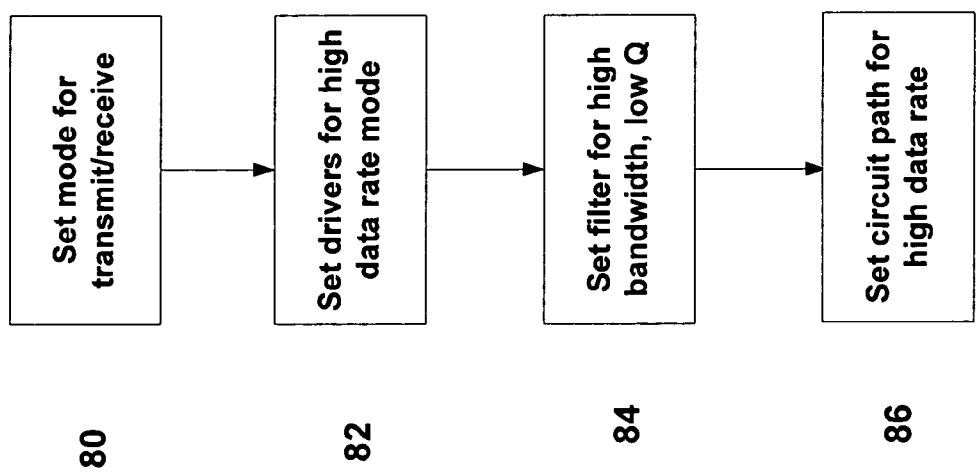
FIG. 6 shows a detailed method for operating programmable telemetry circuitry in a high data rate mode according to an embodiment of the present invention.

A detailed method for operating programmable telemetry circuitry in a high data rate mode according to an embodiment of the present invention is shown in FIG. 6. A high data rate of transmission or reception may be necessary in a variety of applications. For example, if historical data is being transmitted from the telemetry circuitry to another device for data analysis, the data being transmitted may be voluminous. In such an application, a high data rate may be desirable. In addition, if software resident within the telemetry circuitry requires updating, for example, new software being transmitted to the telemetry circuitry could also be voluminous. In such an application, a high data rate may be desirable.

Referring to FIG. 6, at step 80, the telemetry circuitry is set for either transmit or receive mode depending on whether or not data needs to be transmitted or received. At step 82, the low impedance path and the high impedance path are configured such that the low impedance path driver is disabled and the high impedance path driver is enabled so that high data rate is effected. At step 84, the high bandwidth, low Q filter is chosen. At step 86, the circuit path is set for high data rate. Steps 84 and 86 may be implemented in response to a single command or may be implemented in response to multiple commands.

Figure 7:
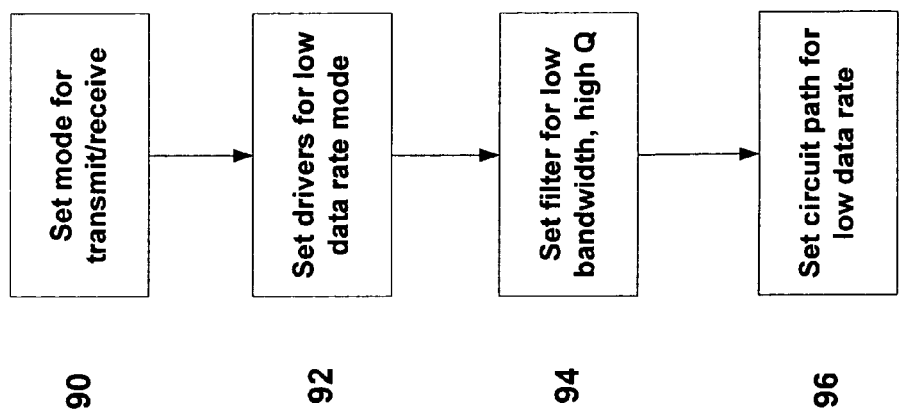
FIG. 7 shows a detailed method for operating programmable telemetry circuitry in a low data rate mode according to an embodiment of the present invention.

FIG. 7 shows a detailed method for operating programmable telemetry circuitry in a low data rate mode according to an embodiment of the present invention. A low data rate of transmission or reception may be necessary in a variety of applications. For example, if the telemetry circuitry is implemented in an implantable medical device having biological or physiological parameter sensors, data from the sensor sent in real time from the telemetry circuitry to an external controller may benefit from a relatively large transmission distance but, given the nature of the sensor, may not require a particularly large bandwidth. Thus, a low data rate mode may be chosen. In addition, if the implanted telemetry circuitry is required to send an alarm to an external controller to indicate an emergency condition in a patient, for example, it would be advantageous for the alarm signal to cover as great a range as possible. In such a situation, the telemetry circuitry may be programmed for a low data rate, thus setting up the telemetry circuit for low bandwidth, high Q transmission.

Referring to FIG. 7, at step 90, the telemetry circuitry is set for transmit or receive mode depending on the desired application. At step 92, the low impedance path driver is enabled, thereby disabling the high impedance path driver and setting the drivers up for low data rate. At step 94, the filters are set for low bandwidth, high Q. At step 96, the circuit path is set for low data rate. Steps 94 and 96 may be implemented in response to a single command or may be implemented in response to multiple commands.

While particular embodiments of the present invention have been shown and described, it will be obvious to those skilled in the art that the invention is not limited to the particular embodiments shown and described and that changes and modifications may be made without departing from the spirit and scope of the appended claims.

What is claimed is:

1. A programmable circuit comprising:
a first coil for transmitting an input signal;
a high impedance path having a first node connected to a first node of the first coil;
a low impedance path having a first node connected to the first node of the first coil, the low impedance path connected in parallel with the high impedance path;
a capacitive path having a first node connected to a second node of the first coil, the capacitive path forming a circuitous path with the high impedance path and the low impedance path;
an input path for coupling signals into the high impedance path, the low impedance path, and the capacitive path,
a second coil having a first node and a second node, the second coil being inductively coupled to the first coil;
a switch having a first node and a second node, the first node of the switch being connected to the first node of the second coil; and
a resistive element having a first node and a second node, the first node of the resistive element being connected to the second node of the switch, the second node of the resistive element being connected to the second node of the second coil,
wherein the programmable circuit is programmed to select the high impedance path or the low impedance path,
wherein the capacitive path includes a low impedance driver, and
wherein closing the switch increases a bandwidth of the programmable circuit.

2. The programmable circuit of claim 1, wherein the high impedance path includes a low impedance driver and a second resistive element.

3. The programmable circuit of claim 2, wherein the second resistive element is a resistor.

4. The programmable circuit of claim 2, wherein the second resistive element is a semiconductor.

5. The programmable circuit of claim 2, wherein the low impedance driver is a semiconductor.

6. The programmable circuit of claim 1, wherein the low impedance path includes a low impedance driver.

7. The programmable circuit of claim 6, wherein the low impedance driver is a semiconductor.

8. The programmable circuit of claim 1, wherein the low impedance driver is a semiconductor.

9. The programmable circuit of claim 1, wherein the capacitive path includes a capacitor.

10. The programmable circuit of claim 1, wherein the first coil is an inductor.

11. The programmable circuit of claim 1, wherein the second coil is an inductor.

12. The programmable circuit of claim 1, wherein the resistive element is a resistor.

13. The programmable circuit of claim 1, wherein the resistive element is a semiconductor.

14. A telemetry circuit having programmable parameters comprising:

a first coil for transmitting and receiving signals;

a high impedance path having a first node connected to a first node of the first coil;

a low impedance path having a first node connected to the first node of the first coil, the low impedance path connected in parallel with the high impedance path;

a capacitive path having a first node connected to a second node of the first coil, the capacitive path forming a circuitous path with the high impedance path and the low impedance path;

a first switch for coupling signals into the high impedance path, the low impedance path, and the capacitive path;

a second switch having a first node and a second node, the first node of the second switch connected to the second node of the first coil;

a high bandwidth, low Q filter having a first node and a second node, the first node of the high bandwidth, low Q filter connected to the second node of the second switch;

a low bandwidth, high Q filter having a first node and a second node, the first node of the low bandwidth, high Q filter connected to the second node of the second switch, wherein the second node of the high bandwidth, low Q filter is connected to the second node of the low bandwidth, high Q filter such that the high bandwidth, low Q filter and the low bandwidth, high Q filter are connected in parallel, wherein the programmable circuit is programmable to select the high impedance path or the low impedance path, and wherein the high bandwidth, low Q filter is selected via the second switch when the high impedance path is selected and the low bandwidth, high Q filter is selected via the second switch when the low impedance path is selected.

15. The telemetry circuit of claim 14, wherein the high impedance path includes a low impedance driver and a resistive element.

16. The telemetry circuit of claim 15, wherein the resistive element is a resistor.

17. The telemetry circuit of claim 15, wherein the resistive element is a semiconductor.

18. The telemetry circuit of claim 15, wherein the low impedance driver is a semiconductor.

19. The telemetry circuit of claim 14, wherein the low impedance path includes a low impedance driver.

20. The telemetry circuit of claim 19, wherein the low impedance driver is a semiconductor.

21. The telemetry circuit of claim 14, wherein the capacitive path includes a low impedance driver.

22. The telemetry circuit of claim 21, wherein the low impedance driver is a semiconductor.

23. The telemetry circuit of claim 21, wherein the capacitive path includes a capacitor.

24. The telemetry circuit of claim 21, wherein the first coil is an inductor.

25. The telemetry circuit of claim 21, further comprising:
a second coil having a first node and a second node, the second coil being inductively coupled to the first coil;
a switch having a first node and a second node, the first node of the switch being connected to the first node of the second coil; and
a resistive element having a first node and a second node, the first node of the resistive element being connected to the second node of the switch, the second node of the resistive element being connected to the second node of the second coil, wherein closing the switch increases a bandwidth of the programmable circuit.

26. A method for modifying circuit parameters of a telemetry circuit comprising:
providing a first coil for transmitting an input signal, the first coil having a first node and a second node;
providing a high impedance path having a first node and a second node;
providing a low impedance path having a first node and a second node, the low impedance path connected in parallel with the high impedance path;
providing a capacitive path having a first node and a second node, the first node of the capacitive path connected to a second node of the first coil;
providing an input path for coupling signals into the high impedance path, the low impedance path, and the capacitive path;
connecting the first node of the first coil to the first node of the high impedance path and the first node of the impedance path;
connecting the first node of the capacitive path to the second node of the first coil;
connecting the capacitive path to the high impedance path and the low impedance path such that the capacitive path forms a circuitous path with the high impedance path and the low impedance path;
enabling either the high impedance path or the low impedance path;
providing a second coil having a first node and a second node;
providing a switch having a first node and a second node;
providing a resistive element having a first node and a second node;
inductively coupling the second coil to the first coil;
connecting the first node of the switch to the first node of the second coil;
connecting the first node of the resistive element to the second node of the switch and the second node of the resistive element to the second node of the second coil; and
closing the switch to increase a bandwidth of the telemetry circuit,
wherein the capacitive path includes a low impedance driver.

27. The method of claim 26, wherein the high impedance path includes a low impedance driver and a second resistive element.

28. The method of claim 27, wherein the second resistive element is a resistor.

29. The method of claim 27, wherein the second resistive element is a semiconductor.

30. The method of claim 27, wherein the low impedance driver is a semiconductor.

31. The method of claim 26, wherein the low impedance path includes a low impedance driver.

32. The method of claim 31, wherein the low impedance driver is a semiconductor.

33. The method of claim 26, wherein the low impedance driver is a semiconductor.

34. The method of claim 26, wherein the capacitive path includes a capacitor.

35. The method of claim 26, wherein the first coil is an inductor.

36. The method of claim 26, further comprising:
providing a high bandwidth, low Q filter having a first node and a second node;
providing a low bandwidth, high Q filter having a first node and a second node;
connecting the first node of the high bandwidth, low Q filter to the second node of the first coil;
connecting the first node of the low bandwidth, high Q filter to the second node of the first coil;
connecting the second node of the high bandwidth, low Q filter to the second node of the low bandwidth, high Q filter such that the high bandwidth, low Q filter and the low bandwidth, high Q filter are connected in parallel;
programming the telemetry circuit to select the high impedance path or the low impedance path; and
programming the telemetry circuit to select the high bandwidth, low Q filter when the high impedance path is selected and the to select the low bandwidth, high Q filter when the low impedance path is selected.

37. The programmable circuit as recited in claim 1, wherein one or more of the first coil, the high impedance path, the low impedance path, the capacitive path, and the input path are provided in an implantable communication device.

38. The programmable circuit as recited in claim 37, wherein the implantable communication device has biological or physiological parameter sensors.

39. The programmable circuit as recited in claim 1, wherein each of the first coil, the high impedance path, the low impedance path, the capacitive path, and the input path are provided in an implantable communication device.

40. The programmable circuit as recited in claim 39, wherein the implantable communication device has biological or physiological parameter sensors.

41. The telemetry circuit having programmable parameters as recited in claim 14, wherein one or more of the first coil, the high impedance path, the low impedance path, the capacitive path, the first switch, the second switch and the low bandwidth are provided in an implantable communication device.

42. The telemetry circuit as recited in claim 41, wherein the implantable communication device has biological or physiological parameter sensors.

43. The telemetry circuit having programmable parameters as recited in claim 14, wherein each of the first coil, the high impedance path, the low impedance path, the capacitive path, the first switch, the second switch and the low bandwidth are provided in an implantable communication device.

44. The telemetry circuit as recited in claim 43, wherein the implantable communication device has biological or physiological parameter sensors.

45. The method of modifying circuit parameters of the telemetry circuit as recited in claim 26, wherein one or more of the first coil, the high impedance path, the low impedance path, the capacitive path, and the input path provided in an implantable communication device.

46. The method of modifying circuit parameters of the telemetry circuit as recited in claim 45, wherein the implantable communication device uses biological or physiological parameter sensors.

47. The method of modifying circuit parameters of the telemetry circuit as recited in claim 26, wherein each of the first coil, the high impedance path, the low impedance path, the capacitive path, and the input path provided in an implantable communication medical device having biological or physiological parameter sensors.

48. The method of modifying circuit parameters of the telemetry circuit as recited in claim 47, wherein the implantable communication device uses biological or physiological parameter sensors.

* * * * *